United States Patent [19]
Sandison et al.

[11] Patent Number: 5,929,985
[45] Date of Patent: Jul. 27, 1999

[54] MULTISPECTRAL IMAGING PROBE

[75] Inventors: David R. Sandison, Moriarty; Mark R. Platzbecker, Albuquerque, both of N.M.; Michael R. Descour, Tucson, Ariz.; David L. Armour; Marcus J. Craig, both of Albuquerque, N.M.; Rebecca Richards-Kortum, Austin, Tex.

[73] Assignee: Sandia Corporation, Albuquerque, N.M.

[21] Appl. No.: 08/820,299

[22] Filed: Mar. 18, 1997

[51] Int. Cl.$^6$ .................................................. G01N 21/63
[52] U.S. Cl. .................................. 356/318; 356/417
[58] Field of Search ..................... 600/591; 250/461.1, 250/462.2, 458.1; 356/318, 301, 417, 418

[56] References Cited

U.S. PATENT DOCUMENTS

| | | | |
|---|---|---|---|
| 5,112,127 | 5/1992 | Carrabba et al. | 356/301 |
| 5,534,997 | 7/1996 | Schrader | 356/301 |
| 5,578,818 | 11/1996 | Kain et al. | 356/328 X |

OTHER PUBLICATIONS

Andrew D. Meigs, Eugene W. Butler, Bernard A. Jones, L. John Otten, III, R. Glenn Sellar, Bruce Rafert, Michael R. Descour and Mooney, Airborne Visible Hyperspectral Imaging Spectrometer: Optical and System Level Description, *SPIE* vol. 2819, p. 278. 1996.

Fiber–optic instrumentation Trims Weeks Off the Wait for Cervical Cancer Test Results, *Inside Sandia*, pp. 4–5, Apr. 1996.

*Primary Examiner*—Frank G. Font
*Assistant Examiner*—Tu T. Nguyen
*Attorney, Agent, or Firm*—V. Gerald Grafe

[57] ABSTRACT

A multispectral imaging probe delivers a range of wavelengths of excitation light to a target and collects a range of expressed light wavelengths. The multispectral imaging probe is adapted for mobile use and use in confined spaces, and is sealed against the effects of hostile environments. The multispectral imaging probe comprises a housing that defines a sealed volume that is substantially sealed from the surrounding environment. A beam splitting device mounts within the sealed volume. Excitation light is directed to the beam splitting device, which directs the excitation light to a target. Expressed light from the target reaches the beam splitting device along a path coaxial with the path traveled by the excitation light from the beam splitting device to the target. The beam splitting device directs expressed light to a collection subsystem for delivery to a detector.

16 Claims, 6 Drawing Sheets

MULTISPECTRAL IMAGING PROBE

This invention was made with Government support under Contract DE-AC04-94AL85000 awarded by the U.S. Department of Energy. The Government has certain rights in the invention.

BACKGROUND OF THE INVENTION

This invention relates to the field of probes for delivering excitation light to and collecting response light from a target for spectral analysis.

Many materials express light when excited by incident light. The characteristics of expressed light in response to various excitation light wavelengths can identify the material. Different response spectra can also identify different material properties, as for example in cervical cells where precancerous cells have different response spectra than normal cells. See, e.g., Romanujam et al., U.S. Pat. No. 5,421,339.

Some current spectral imaging systems mount with a laboratory microscope. See, e.g., Fluorescence Imaging Spectroscopy, and Microscopy, Wang and Herman editors, 1996, Chapter 5. Laboratory microscope imaging systems add a high power light source, optics, and detection hardware to a conventional laboratory microscope. These systems are well suited for imaging samples suitable for examination on a microscope stage. They can not, however, image large targets, support in situ imaging, or allow imaging in confined spaces. They are also not suitable for use in hostile environments such as under water, in outer space, or in the presence of hazardous gases.

Other current spectral imaging systems mount as part of a large mobile platform. See, e.g., Airborne Visible Hyperspectral Imaging Spectrometer: Optical and System Level Description, in Imaging Spectrometry II, Meigs, Butler, Jones, Otten, Sellar, Rafert, Descour and Mooney editors, SPIE volume 2819 page 278, 1996. These systems are often used for satellite imaging of the earth using sunlight as the excitation light. They can be designed for use in certain hostile environments. They are not capable, however, of high resolution spectral imaging because they do not have control over the distance to the target and do not generate selectable wavelength excitation light. They can image very large targets, but are not capable of precisely imaging areas less than tens of meters at a time. They also are not capable of imaging in confined spaces or of imaging various aspects of a target.

Many materials whose properties are of interest can not be moved. For example, cells attached or within a body must be either biopsied (an invasive procedure) or imaged in situ. Materials embedded in structures such as pipelines must be imaged in situ. Often, materials to be imaged can only be accessed in a confined space. Examples include cervical cells and the interior of enclosed structures. Determining properties of materials located in hazardous environments can pose danger to humans making the determination.

There is therefore a need for a multispectral imaging probe that can deliver a range of wavelengths of excitation light to a target and collect a range of expressed light wavelengths, that is adapted for mobile use and use in confined spaces, and that is sealed against the effects of hostile environments.

SUMMARY OF THE INVENTION

The present invention provides a multispectral imaging probe that can deliver a range of wavelengths of excitation light to a target and collect a range of expressed light wavelengths. The multispectral imaging probe is adapted for mobile use and use in confined spaces, and is sealed against the effects of hostile environments. The multispectral imaging probe comprises a housing that is substantially sealed from the surrounding environment. A beam splitting apparatus mounts within the sealed housing. Excitation light is directed to the beam splitting apparatus, which directs the excitation light to a target. Expressed light from the target propagates to the beam splitting apparatus along a path coaxial with the path traveled by the excitation light from the beam splitting apparatus to the target. The beam splitting apparatus directs expressed light to a collection subsystem for delivery to a detector.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

Figure 1:
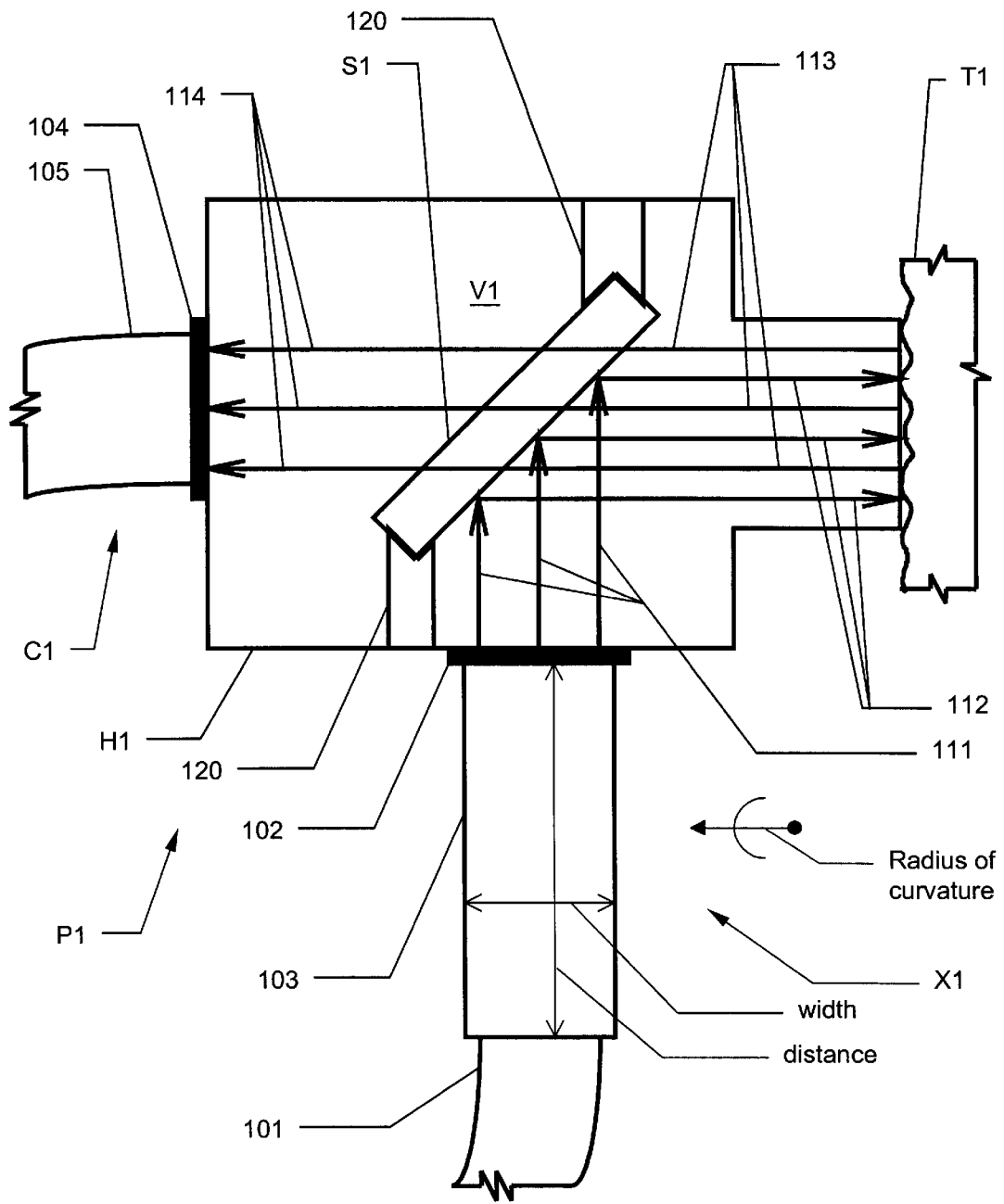
FIG. 1 is sectional view of a multispectral imaging probe according to the present invention.

FIG. 1 is a sectional view of a multispectral imaging probe P1 according to the present invention. Probe P1 directs excitation light received from a light source (not shown) via excitation subsystem X1 to target T1 along an optical path represented by lines 111, 112. Probe P1 directs expressed light from target T1 to collection subsystem C1 along an optical path represented by lines 113, 114. Probe P1 includes a housing H1 which defines a substantially sealed volume V1. The sealed volume V1 prevents entry of contaminants that can interfere with accurate spectral imaging. It also prevents the exit of contaminants, from the components therein or from previous uses of probe P1, that can contaminate subsequent targets. The sealed volume V1 can also provide for containment of an inert gas (not shown) if desired for performance or safety considerations.

Beam splitting apparatus S1 mounts within volume V1. In FIG. 1, protrusions 120 from housing H1 hold beam splitting apparatus S1 in volume V1. Those skilled in the art will appreciate other ways of mounting beam splitting apparatus S1 within volume V1. Collection subsystem C1 mounts with housing H1, defining a first optical path having two parts: a first part 113 from target T1 to beam splitting apparatus S1, and a second part 114 from beam splitting apparatus S1 to collection subsystem C1. Excitation subsystem X1 mounts with housing H1, defining a second optical path having two parts: a first part 111 from excitation subsystem X1 to beam splitting apparatus S1, and a second part 112 from beam splitting apparatus S1 to target T1. The parts 112, 113 between beam splitting apparatus S1 and target T1 of the first and second optical paths are coaxial. Those skilled in the art will appreciate that the location of excitation subsystem X1 and collection subsystem C1 relative to beam splitting apparatus S1 depends on the characteristics of beam splitting apparatus S1; they can be as shown in FIG. 1, transposed, or mounted at various angles.

Beam splitting apparatus S1 can be chosen so that it will reflect light having certain properties and transmit light having other properties. For example, dichroic mirrors reflect light having certain wavelengths and transmit light having other wavelengths. As another example, partially reflective mirrors can direct a portion of the excitation light to the target while allowing a portion of the expressed light to reach the collection subsystem, even if the expressed light and excitation light have the same wavelengths. As a further example, a polarizing beam splitter can direct excitation light to the target and expressed light to the collection subsystem if the excitation light and expressed light have distinguishable polarizations. A pelical beam splitter is another example of a suitable beam splitting device. Beam splitting apparatus S1 can be chosen so that it reflects excitation light on path 111, for example, and directs it to target T1 along path 112, and so that it transmits expressed light on path 113 from target T1 to collection subsystem C1 along path 114.

Excitation subsystem X1 directs excitation light, represented generally by lines 111, 112, to beam splitting apparatus S1. Excitation light can be generated by an external source (not shown) and transmitted to probe P1 by a first transmissive conduit 101 such as a flexible light guide. Handle 103 extending from housing H1 can allow a user to hold probe P1 and can help prevent sharp bends that can reduce the efficiency of flexible light guides. For example, handle 103 can extend from housing H1 approximately three times the width of handle 103, and can have a radius of curvature at least three times the width of handle 103, to support a flexible light guide while preventing sharp bends therein. A lens 102 can be used to focus excitation light 111, 112 from first transmissive conduit 101 through beam splitting apparatus S1 onto target T1. Alteratively, the shape, orientation, and physical characteristics of first transmissive conduit 101 and its mounting with housing H1 can direct excitation light 111, 112 to beam splitting apparatus S1.

Collection subsystem C1 receives expressed light 113, 114 from target T1 through beam splitting apparatus S1. Second transmissive conduit 105 can transmit expressed light 113, 114 from probe P1 to an external detector (not shown). A lens 104 can focus an image of target T1 onto second transmissive conduit 105 for transmission. Alternatively, the characteristics of second transmissive conduit 105 and its mounting with housing H1 can image target T1 into second transmissive conduit 105 without a separate lens 104.

Housing H1 can be made from plastic, magnesium, and stainless steel, for example. Probe P1 should be light for convenient hand held operation. Probe P1's exterior shape (not shown) can be contoured to fit in confined spaces if the intended use so requires. The overall size of probe P1 can be minimized to fit in confined spaces and to avoid bulkiness that can complicate hand held operation. The location of optical components such as beam splitting apparatus S1 and lenses 102, 104 can be critical to accurate imaging, so housing H1 must be structurally capable of precise mounting. Flexible light guides allow mobile use, but sharp bending can cause reduced light transmission efficiency and therefor limitations on input excitation power and on minimum detectable expressed light power can impose constraints on mobility of probe P1.

Figure 2A:
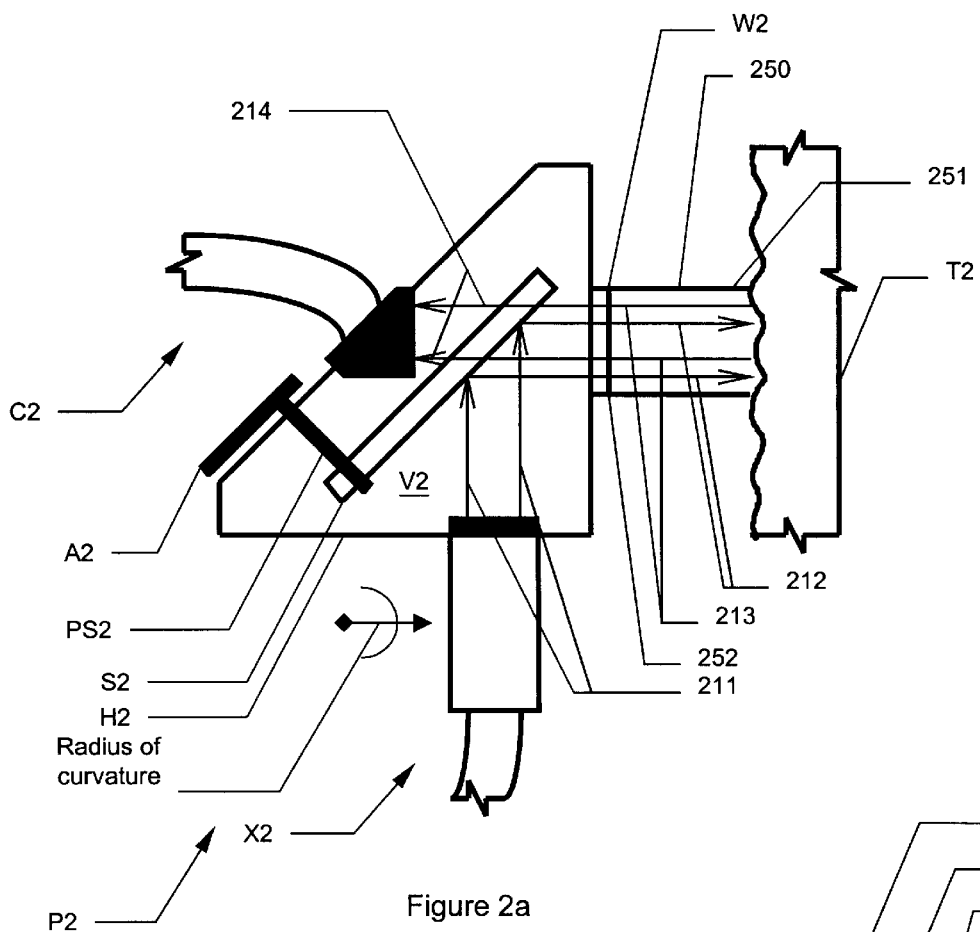
FIG. 2a is sectional view of a multispectral imaging probe according to the present invention.

FIG. 2a is a sectional view of a multispectral imaging probe P2 according to the present invention. Probe P2 directs excitation light from excitation subsystem X2 to target T2. Probe P2 directs expressed light from target T2 to collection subsystem C2. Probe P2 includes housing H2 which defines a substantially sealed volume V2. The sealed volume V2 prevents entry of contaminants that can interfere with accurate spectral imaging. It also prevents the exit of contaminants, from the components therein or from previous uses of probe P2, that can contaminate subsequent targets.

Beam splitting apparatus S2 mounts within volume V2. Collection subsystem C2 mounts with housing H2, defining a first optical path having two parts: a first part 213 from target T2 to beam splitting apparatus S2, and a second part 214 from beam splitting apparatus S2 to collection subsystem C2. Excitation subsystem X2 mounts with housing H2, defining a second optical path having two parts: a first part 211 from excitation subsystem X1 to beam splitting apparatus S2, and a second part 212 from beam splitting apparatus S2 to target T2. The parts 212, 213 of the first and second optical paths between beam splitting apparatus S2 and target T2 are coaxial. Those skilled in the art will appreciate that the location of excitation subsystem X2 and collection subsystem C2 relative to beam splitting apparatus S2 depends on the characteristics of beam splitting apparatus S2; they can be as shown in FIG. 2, transposed, or mounted at various angles.

Extension 250 mounts with housing H2 and extends therefrom along the coaxial parts of the first and second optical paths 212, 213 (the "propagation axis"). Distal end 251 of extension 250 can be adapted to maintain a predetermined distance from beam splitting apparatus S2 to target T2. The focal distance from excitation subsystem X2 and collection subsystem C2 to target T2 can thereby be maintained at a predetermined length. Extension 250 can be permanently or removably mounted with housing H2.

Extension 250 can transmit light having the same characteristics as excitation light (e.g., wavelength or polarization) and light having the same characteristics as expressed light (e.g., wavelength or polarization) along directions substantially parallel to the propagation axis and can block light not having those characteristics and light having those characteristics but not traveling along the propagation axis. Transmission along the propagation axis is required for excitation light to reach target T2 and expressed light to reach collection subsystem C2. Inhibiting transmission not along the propagation axis can prevent excitation of target T2 by stray light and can prevent collection of light not expressed by target T2. Inhibiting transmission along the propagation axis of light not having the proper characteristics can prevent overloading the detector (not shown) with extraneous light.

For example, extension 250 can circumscribe a hollow interior portion, where gas such as air in the hollow interior space has the desired transmissive properties. Extension 250 can be made from plastic, metal, and glass, for example, or other material having the desired transmissive characteristics. The outer walls of extension 250 can be coated with a material that inhibits light transmission therethrough.

Window W2 mounts with proximal end 252 of extension 250. Window W2 maintains the seal of housing H2 defining volume V2. Window W2 can be chosen so that undesired reflections and transmissive losses are minimized. Window W2 can mount with housing H2 so that extension 250 can be removed without removing window W2, thereby maintaining the seal. Alternatively, window W2 can be removably mounted with housing H2 to allow access to the interior of housing H2.

Figure 2B:
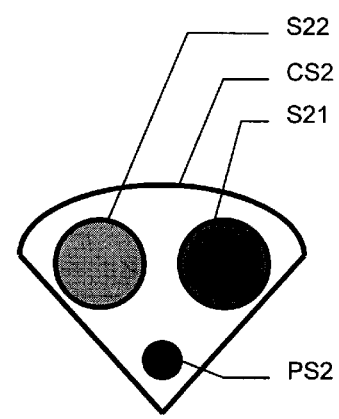
FIG. 2b is an illustration of a beam splitting apparatus according to the present invention.

FIG. 2b is an illustration of beam splitting apparatus S2. Beam splitting apparatus S2 can comprise multiple beam splitting devices S21, S22 mounted with carrier CS2. Carrier CS2 and post PS2 mount within volume V2 so that carrier CS2 is moveable among several positions. At one position, beam splitting device S21 is held in the path of excitation light and expressed light. At another position, beam splitting device S22 is held in the path of excitation light and expressed light. The availability of a plurality of beam splitting devices S21, S22 can allow spectral imaging with a wider range of excitation light and expressed light characteristics (such as wavelength or polarization).

Carrier CS2 mounts with post PS2 so that rotation of post PS2 moves carrier CS2 within volume V2. Post PS2 can extend through housing H2 to allow actuation outside volume V2 to effect movement of carrier CS2. For example, lever A2 can mount with post PS2 outside volume V2 so that rotation of lever A2 about post PS2 causes movement of carrier CS2. Alternatively, carrier CS2 can be moved by electromagnetic or other actuators within volume V2. Sealed mounting of post PS2 with housing H2 allows selection among a plurality of beam splitting devices S21, S22 without breaking the seal around volume V2.

Figure 3A:
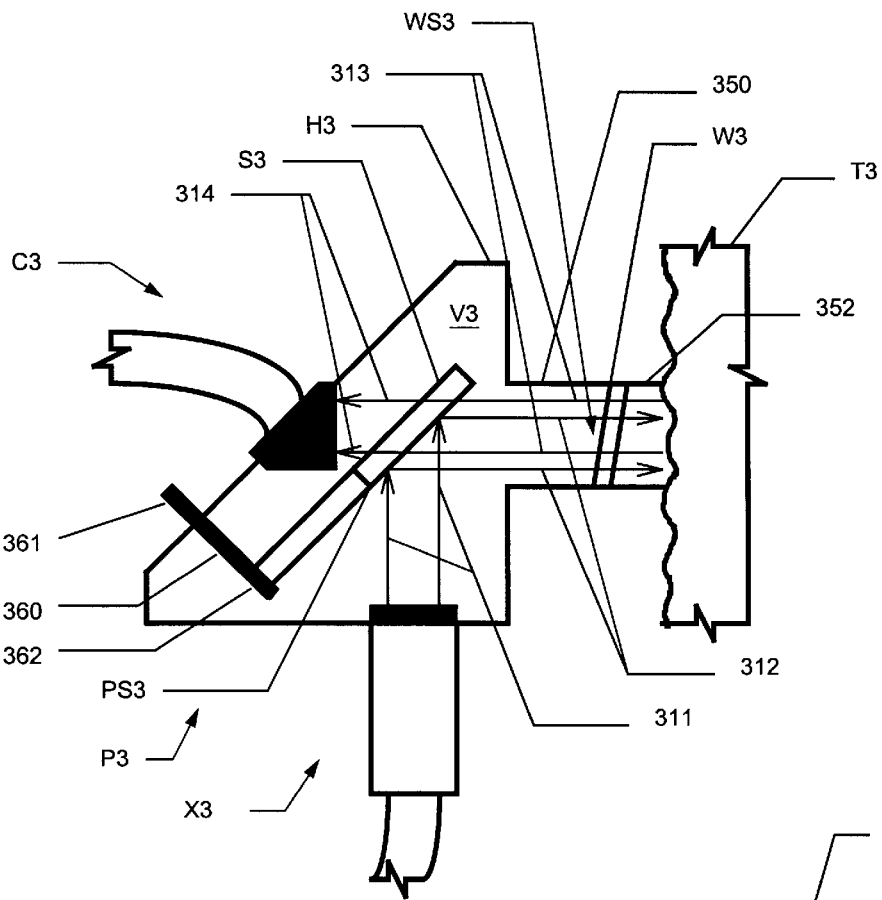
FIG. 3a is sectional view of a multispectral imaging probe according to the present invention.

FIG. 3a is a sectional view of a multispectral imaging probe according to the present invention. Probe P3 directs excitation light from excitation subsystem X3 to target T3. Probe P3 directs expressed light from target T3 to collection subsystem C3. Probe P3 includes housing H3 which defines a substantially sealed volume V3. The sealed volume V3 prevents entry of contaminants that can interfere with accurate spectral imaging. It also prevents the exit of contaminants, from the components therein or from previous uses of probe P3, that can contaminate subsequent targets.

Beam splitting apparatus S3 mounts within volume V3. Collection subsystem C3 mounts with housing H3, defining a first optical path having two parts: a first part 313 from target T3 to beam splitting apparatus S3, and a second part 314 from beam splitting apparatus S3 to collection subsystem C3. Excitation subsystem X3 mounts with housing H3, defining a second optical path having two parts: a first part 311 from excitation subsystem X3 to beam splitting apparatus S3, and a second part 312 from beam splitting apparatus S3 to target T3. The parts 312, 313 of the first and second optical paths between beam splitting apparatus S3 and target T3 are coaxial. Those skilled in the art will appreciate that the location of excitation subsystem X3 and collection subsystem C3 relative to beam splitting apparatus S3 depends on the characteristics of beam splitting apparatus S3; they can be as shown in FIG. 3, transposed, or mounted at various angles.

Extension 350 mounts with housing H3 and extends therefrom along the coaxial parts of the first and second optical paths 312, 313 (the "propagation axis"). Extension 350 can maintain focal distances as discussed for extension 250 of FIG. 2. Extension 350 can have transmissive properties as described for extension 250 of FIG. 2. Extension 350 can be permanently or removably mounted with housing H3.

Window W3 mounts with distal end 352 of extension 350. Window W3 maintains the seal of housing H3 defining volume V3. Window W3 can be chosen so that undesired reflections and transmissive losses are minimized. Window W3 can mount with housing H3 so that extension 350 can be removed without removing window W3, thereby maintaining the seal. Alternatively, window W3 can be mounted with extension 350 and removed therewith. Window W3 can be mounted so that surface WS3 in light paths along the propagation axis is at an angle other than 90 degrees to the propagation axis so that reflections from surface WS3 are not parallel to the propagation axis and transmission thereof inhibited by extension 350.

Figure 3B:
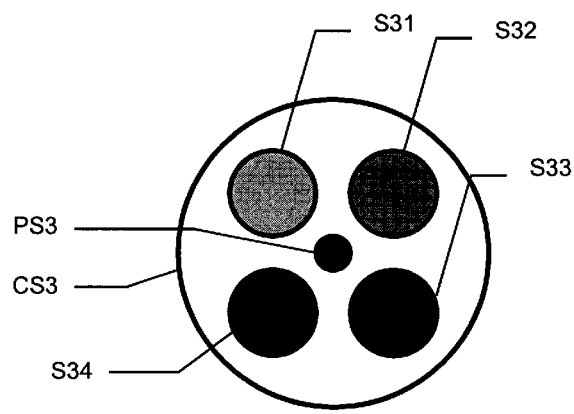
FIG. 3b is an illustration of a beam splitting apparatus according to the present invention.

FIG. 3b is an illustration of beam splitting apparatus S3. Beam splitting apparatus S3 can comprise multiple beam splitting devices S31, S32, S33, S34 mounted with carrier CS3. Carrier CS3 and post PS3 mount within volume V3 so that carrier CS3 is moveable among several positions. At one position, beam splitting device S31 is held in the path of excitation light and expressed light. At other positions, beam splitting devices S32, S33, S34 are alternately held in the path of excitation light and expressed light. The availability of a plurality of beam splitting devices can allow spectral imaging with a wider range of excitation light and expressed light characteristics (such as wavelength or polarization).

Carrier CS3 mounts with post PS3 so that rotation of post PS3 rotates carrier CS3 within volume V3. Post PS3 can extend through housing H3 to allow actuation outside volume V3 to effect movement of carrier CS3. Alternatively, thumbwheel 360 can mount with carrier CS3 so that motion of thumbwheel 360 causes rotation of carrier CS3 about post PS3. A first portion 361 of thumbwheel 360 extends outside volume V3 for actuation. A second portion 362 of thumbwheel 360 engages carrier CS3 inside volume V3. As another alternative, carrier CS3 can be rotated by an actuator such as a stepper motor within volume V3.

Figure 4:
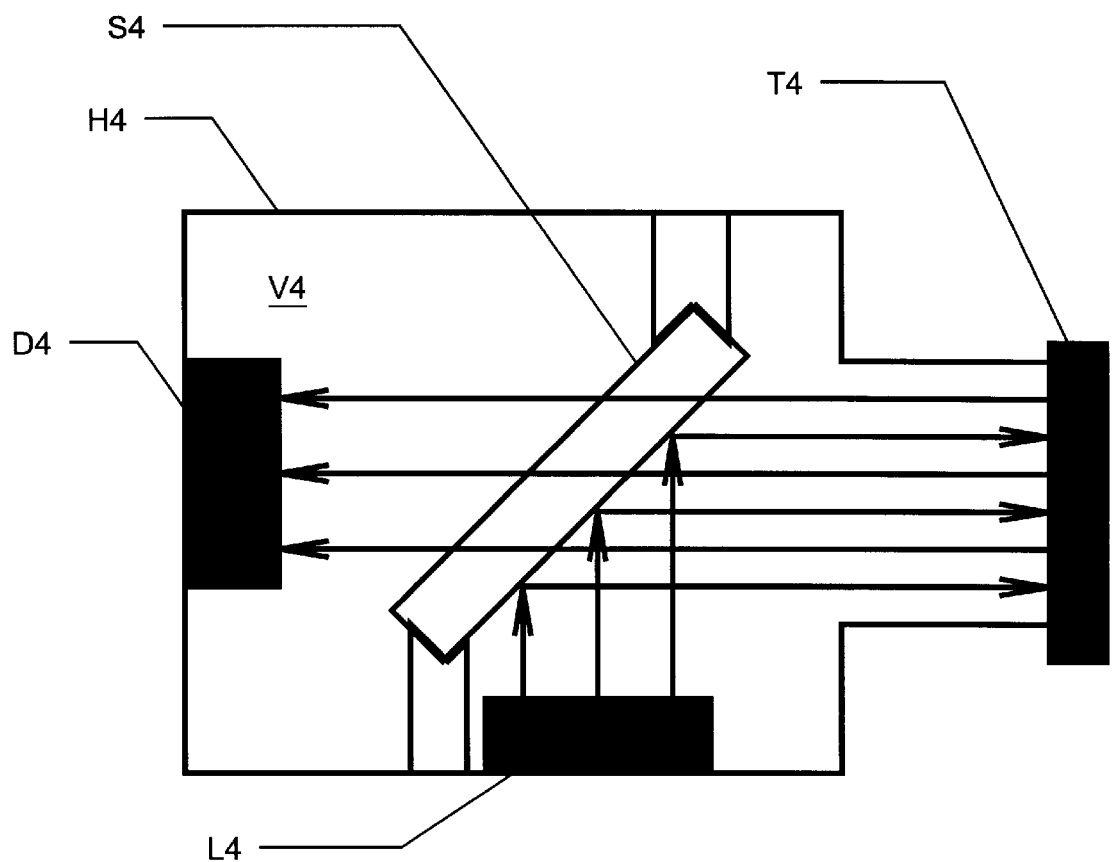
FIG. 4 is sectional view of a multispectral imaging probe according to the present invention.

FIG. 4 is a sectional view of a multispectral imaging probe according to the present invention. The mounting and function of housing H4, volume V4, and beam splitting apparatus S4 are as described generally for FIGS. 1, 2, and 3. Light source L4 generates excitation light and directs it to beam splitting apparatus S4. Detector D4 detects the intensity of expressed light from target T4 directed thereto by beam splitting apparatus S4. Intensity measurements from detector D4 can be transmitted by wire, radio, or other means to a remote analysis system (not shown) or can be stored at the probe P4 for later analysis. Placement of detector D4 and light source L4 with probe P4 can make probe P4 more mobile by relaxing constraints on motion due to light guides, but can also increase the weight of probe P4 due to the addition of light source L4 and detector D4 and associated power supplies.

Figure 5:
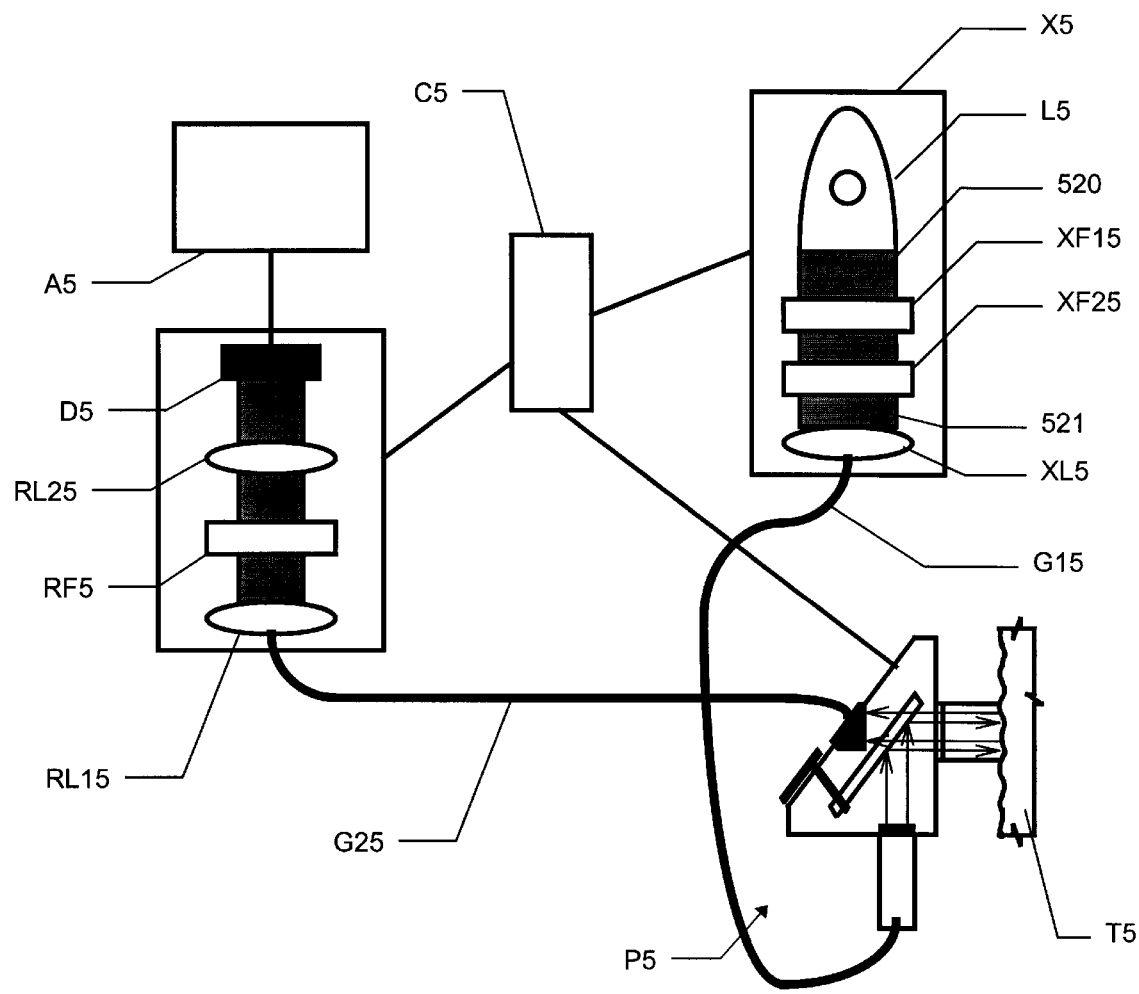
FIG. 5 is a block diagram of a multispectral imaging system employing a multispectral imaging probe according to the present invention.

FIG. 5 is a block diagram of a multispectral imaging system employing a multispectral imaging probe P5 according to the present invention. An excitation source X5 comprises a lamp L5, two filters XF15, XF25, and a lens XL5. For imaging an entire cervix in one to ten seconds, lamp L5 can deliver about 10 mW power at each excitation wavelength and the wavelength selection time can be about one second. As an example, a 300 W xenon arc lamp with a built-in parabolic reflector can deliver over 40 mW/nm output power in the wavelength range from 300 nm to 2000 nm. The parabolic reflector can collect light more efficiently than condensor/reflector geometries. Integrating the reflector into the lamp can also obviate the alignment problems that accompany conventional lamp housings.

Interference filters can select wavelengths from the parabolic reflector's nearly collimated output. Filter XF15 can be an infrared filter to reject heat energy in the light beam output of lamp L5. Filter XF15 can remove near infrared light (approximately from 800 nm to 2000 nm) that could otherwise heat and damage other parts of the apparatus. As an example, KG1 glass such as that made by Schott Glass Technologies of Duryea, Pa., can be used as filter XF15. KG1 glass absorbs strongly in the near infrared, and dissipates the energy as heat. A KG1 filter XF15 can be radially symmetric and can be aligned along the optic axis of lamp L. Other examples of suitable filters XF15 include water mirrors, infrared reflecting filters, and infrared transmitting mirrors.

Filter XF25 can be a filter wheel, controlled by a controller C5 to select specific excitation wavelengths for target excitation. Interference filters with bandwidths on the order of 10 nm can be used. Filter XF25 preferably does not fluoresce or otherwise emit light that might be confused with expressed light from target T5. Filter XF25 preferably adequately blocks light outside the filter's pass band, which can be from 2 nm to 200 nm wide.

Light 521 from filters XF15, XF25 can be focused into a first transmissive conduit G15 by lens XL5. A condenser lens can be used as lens XL5. A liquid light guide is an example of a suitable first transmissive conduit G15. The liquid light guide can have an input aperture approximately 3 mm in diameter to avoid alignment problems common to small diameter optical fibers. First transmissive conduit G15 delivers the light energy to a probe P5 adapted for illuminating a target T5. Probe P5 can be a multispectral imaging probe such as those previously described.

Second transmissive conduit G25 transmits expressed light from target T5 and collected by probe P5. A coherent optical fiber bundle is an example of a suitable second transmissive conduit G25. The fiber density in the bundle must be high enough to preserve the image. The fibers in the bundle also must transmit the wavelengths of interest.

Light from second transmissive conduit G25 can be focused by lens RL15 onto a filter RF5. Lens RL15 can collimate the real image transmitted by a coherent optical fiber bundle. Filter RF5 can be a filter wheel, controlled by controller C5, to select specific response wavelengths of interest in the target's response. Light from filter RF5 can be focused onto a detector D5 by lens RL25. Detector D5 preferably preserves the cross section information of the expressed light from target T5. A CCD imaging detector is an example of a suitable detector D5. A CCD imaging detector converts photons to an analog voltage proportional to the integrated intensity at each pixel, where each pixel corresponds to a portion of the image focused onto detector D5. Detector D5 can output signals representative of the target's response at specific response wavelengths to excitation by light of specific excitation wavelengths. The signals from the detector D5 can be used by analysis means A5 to determine target properties, including detection of cell abnormalities, as discussed above.

Figure 6:
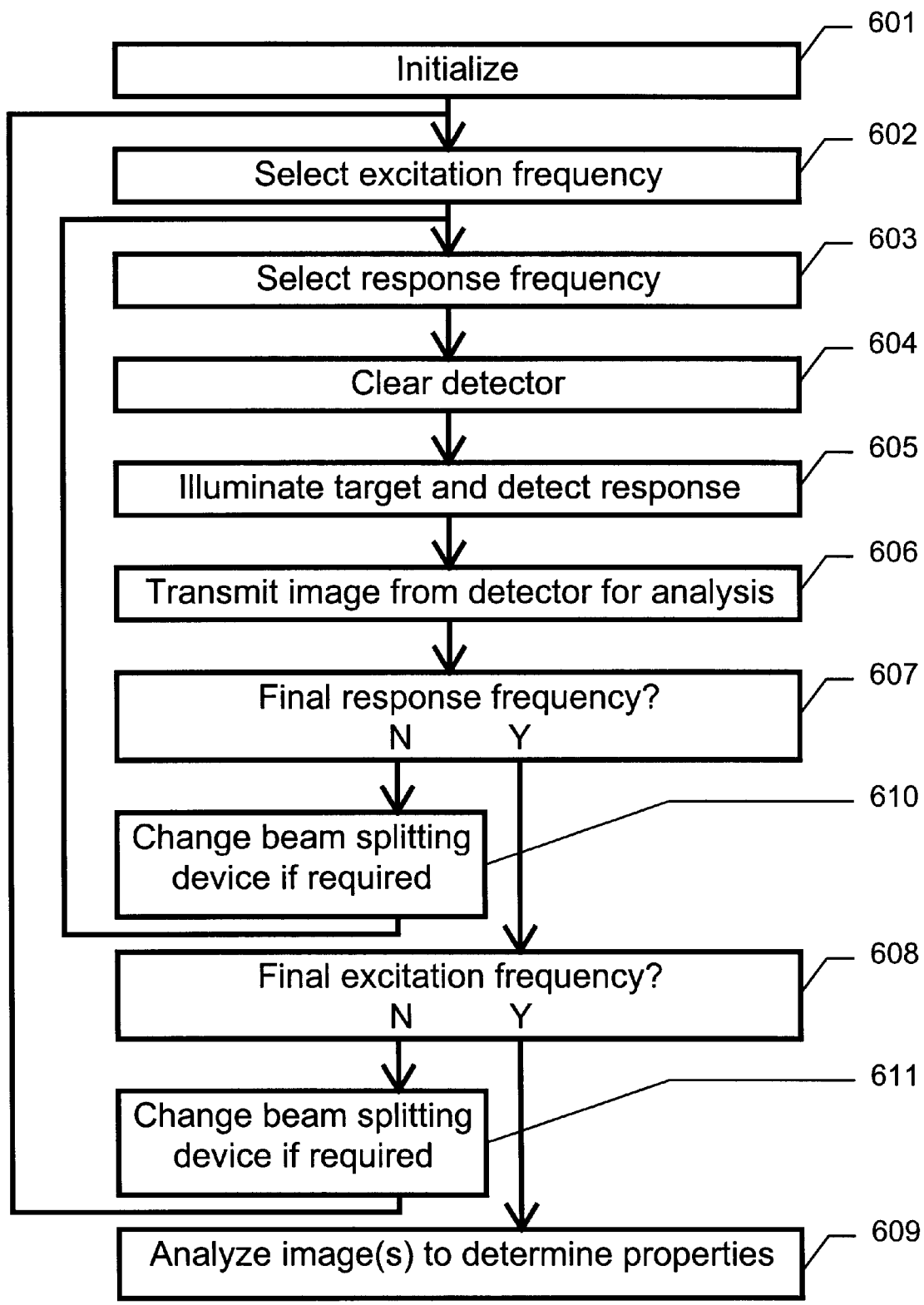
FIG. 6 is a flow diagram of the control of a multispectral imaging system employing a multispectral imaging probe according to the present invention.

FIG. 6 is a flow diagram of the control of a multispectral imaging system according to the present invention. Any components of the system that need initialization are first initialized 601. An excitation wavelength is selected 602, for example by rotating a filter wheel. A response wavelength is selected 603, for example by rotating a filter wheel. The detector is cleared of any previous response information 604. The target is then illuminated with the selected excitation wavelength and the response at the selected response wavelength detected 605. The image from the detector of the target's response is transmitted for analysis 606. If this is not the final response wavelength to be detected 607, then a new response wavelength is selected 603 and the process repeated from there. If a different beam splitting device is required at the probe for the new response wavelength, then a signal is generated to cause the selection of a new beam splitting device 610. For example, a lamp can be flashed or an indicator displayed to prompt an operator to change the beam splitting means, or electrical signals can cause automatic actuators to change the beam splitting device. If this is not the final excitation wavelength 608, then a new excitation wavelength is selected 602 and the process repeated from there. If a different beam splitting apparatus is required at the probe for the new excitation wavelength, then a signal is generated as discussed above to cause the selection of a new beam splitting apparatus 611. After all the response wavelength/excitation wavelength pairings have been detected, then the images are analyzed to determine the cell properties 609. Note that the order of response frequency and excitation frequency selection could be reversed.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A multispectral imaging probe for directing excitation light to a target and directing expressed light from the target to a detector, comprising:

a) a housing defining a substantially sealed volume;

b) splitting means for directing excitation light and expressed light;

c) mounting means for mounting the splitting means within the sealed volume so that excitation light incident thereon is directed by the splitting means to the target along a propagation axis and expressed light from the target travels to the splitting means on an expressed light path along the propagation axis;

d) excitation means for directing excitation light along an excitation light path to the splitting means; and e) collection means for directing expressed light from the splitting means to the detector, where the excitation means comprises a flexible light guide, where the housing additionally comprises a handle extending along a path a first distance and having a first width measured orthogonal to the path of extension, where the first distance is at least three times the first width and where the radius of curvature of the path is at least three times the first width, and where the flexible light guide is mounted with the handle.

2. A multispectral imaging probe for directing excitation light to a target and directing expressed light from the target to a detector, comprising:

a) a housing defining a substantially sealed volume;

b) splitting means for directing excitation light and expressed light;

c) mounting means for mounting the splitting means within the sealed volume so that excitation light incident thereon is directed by the splitting means to the target along a propagation axis and expressed light from the target travels to the splitting means on an expressed light path along the propagation axis;

d) excitation means for directing excitation light along an excitation light path to the splitting means; and e) collection means for directing expressed light from the splitting means to the detector, where the mounting means comprises a carrier adapted to hold a plurality of splitting devices, said carrier moveably mounted with the housing and moveable among a plurality of positions, where each splitting device is in the excitation light path and in the expressed light path when the carrier is in one of the plurality of positions.

3. The probe of claim 2, where the excitation means comprises a lens mounted with the housing so that excitation light is focused through the splitting means onto the target.

4. The probe of claim 2, where the mounting means additionally comprises:
   a) a post rotatably mounted with the housing having a first end outside the sealed volume and a second end inside the sealed volume, where said carrier is mounted with the second end so that rotation of the post causes the carrier to move among the plurality of positions; and
   b) an actuator mounted with the first end of the post so that motion of the actuator causes rotation of the post.

5. The probe of claim 2, where the mounting means comprises:
   a) an extension mounted with the housing and extending therefrom along the propagation axis; and
   b) means for mounting the splitting means a first predetermined distance from the distal end of the extension, where the distal end of the extension portion is adapted to maintain a second predetermined distance from the splitting means to the target.

6. The probe of claim 5, where the extension transmits light having the same characteristics as the excitation light and light having the same characteristics as the expressed light along directions substantially parallel to the propagation axis and does not transmit light having the same characteristics as the excitation light and light having the same characteristics as the expressed light along directions not substantially parallel to the propagation axis.

7. The probe of claim 5, where the extension comprises a wall extending along the direction of the propagation axis and circumscribing a hollow interior.

8. The probe of claim 5, where the extension additionally comprises sealing means for preventing fluid communication into the sealed volume.

9. The probe of claim 8, where the sealing means comprises a window that transmits light having the same wavelength as the excitation light and light having the same wavelength as the expressed light along directions parallel to the propagation axis.

10. The probe of claim 9, where the window is mounted with the distal end of the extension.

11. The probe of claim 9, where the window is mounted with the proximal end of the extension.

12. The probe of claim 9, where the window is mounted with the extension so that a first surface of the window is in the light path from the splitting means to the target, and where the first surface is at an angle other than 90 degrees to the propagation axis.

13. The probe of claim 5, where the housing additionally comprises means for removeably mounting the extension.

14. A multispectral imaging probe for directing excitation light to a target and directing expressed light from the target to a detector, comprising:
   a) a housing defining a substantially sealed volume;
   b) splitting means for directing excitation light and expressed light;
   c) mounting means for mounting the splitting means within the sealed volume so that excitation light incident thereon is directed by the splitting means to the target along a propagation axis and expressed light from the target travels to the splitting means on an expressed light path along the propagation axis;
   d) excitation means for directing excitation light along an excitation light path to the splitting means; and
   e) collection means for directing expressed light from the splitting means to the detector, where the collection means comprises a flexible image preserving light guide.

15. The probe of claim 14, where the collection means additionally comprises a lens mounted with the housing so that expressed light is focused from the target onto the flexible light guide.

16. A multispectral imaging probe for directing excitation light to a target and directing expressed light from the target to a detector, comprising:
   a) a housing defining a substantially sealed volume, and comprising a handle extending along a path a first distance and having a first width measured orthogonal to the path of extension, where the first distance is at least three times the first width and where the radius of curvature of the path is at least three times the first width;
   b) splitting means for splitting a light beam,
   c) mounting means for mounting the splitting means within the sealed volume so that excitation light incident thereon is directed by the splitting means to the target along a propagation axis and expressed light from the target travels to the splitting means on an expressed light path along the propagation axis, where the mounting means comprises a carrier adapted to hold a plurality of splitting devices, said carrier moveably mounted with the housing and moveable among a plurality of positions, where each splitting device is in the excitation light path and in the expressed light path when the carrier is in one of the plurality of positions;
   d) a first flexible light guide mounted with the handle oriented so that light from the first flexible light guide is directed therefrom to the splitting means; and
   e) collection means for directing expressed light from the splitting means to the detector.

* * * * *